(12) United States Patent
James et al.

(10) Patent No.: US 6,627,594 B1
(45) Date of Patent: Sep. 30, 2003

(54) PEROXY-CARBOXYLIC ACID AND AQUEOUS COMPOSITIONS THEREOF

(75) Inventors: Alun P. James, Liverpool (GB); John P. Sankey, Cheshire (GB)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 10/009,993

(22) PCT Filed: Jun. 7, 2000

(86) PCT No.: PCT/EP00/05307

§ 371 (c)(1),
(2), (4) Date: Apr. 3, 2002

(87) PCT Pub. No.: WO00/76963

PCT Pub. Date: Dec. 21, 2000

(30) Foreign Application Priority Data

Jun. 14, 1999 (EP) .............................. 99304611

(51) Int. Cl.$^7$ ...................... C11D 3/395; C07C 409/00

(52) U.S. Cl. ...................... 510/375; 510/372; 510/310; 568/568

(58) Field of Search ................. 510/375, 372, 510/310; 568/568

(56) References Cited

FOREIGN PATENT DOCUMENTS

| WO | 93 05016 | 3/1993 |
|---|---|---|
| WO | 95/34537 | 12/1995 |
| WO | 98/28267 | 7/1998 |
| WO | WO 00/27973 | * 5/2000 |

* cited by examiner

Primary Examiner—Mark Kopec
Assistant Examiner—John M. Petruncio
(74) Attorney, Agent, or Firm—Oblon, Spivak, McClelland, Maier & Neustadt, P.C.

(57) ABSTRACT

The invention concerns compound HO—$(CH_2)_5$—COOOH or 6-hydroxypercaproic acid, its preparation process, i.e. from ε-caprolactone, aqueous compositions thereof and their use as disinfectant or bleaching agents.

24 Claims, No Drawings

PEROXY-CARBOXYLIC ACID AND AQUEOUS COMPOSITIONS THEREOF

This invention relates to a new peroxy-carboxylic acid, to aqueous compositions containing percarboxylic acids and more specifically to their preparation and their use for disinfection.

Percarboxylic acids (peracids), by virtue of their properties, are contemplated for application in a wide range of uses, for example as oxidants, as stain removers and as microbicides, amongst others. The most well known prior art percarboxylic acid equilibrium solutions contain peracetic or perglutaric acid. The former is a very effective biocide, but it suffers from having an unpleasant odor, even in very dilute form. Perglutaric acid has no odor, but suffers from poorer biocidal properties than peracetic acid, especially at pH>3, and on yeasts. Other odourless peracid solutions have been described based on a wide range of acids (i.e. citric, lactic, succinic, adipic acids etc), all of these peracids are either unstable in solution (i.e. lactic) or have limited biocidal properties.

As an alternative to compositions containing peracetic acid or perglutaric acid, WO 95/34537 and WO 98/28267 to Solvay Interox Limited reveal compositions based on ester peracids which have a low odor and effective biocidal properties, over a range of conditions.

It is an object of the present invention to provide a new peroxy-carboxylic acid. According to another aspect of the present invention there is provided to provide a new and effective process for preparing aqueous peracid compositions, without unpleasant odor and with good level of biocidal performance. Other objects of the present invention relate to the storage-stable aqueous peracid compositions and their use as a disinfectant.

According to the present invention there is provided a new percarboxylic acid compound, viz. compound of formula $HO-(CH_2)_5-CO_3H$, which is also referred to in this text as 6-hydroxypercaproic acid.

In a further aspect, this invention provides a process for preparing aqueous percarboxylic acid compositions, which process comprises contacting a precursor of 6-hydroxypercaproic acid with a peroxygen compound.

In a particularly preferred embodiment, the precursor of 6-hydroxypercaproic acid is ϵ-caprolactone or water soluble dimers and/or oligomers thereof The special advantage of using ϵ-caprolactone is due to its high solubility in aqueous media.

In a further embodiment of the present invention, 6-hydroxypercaproic acid is obtained directly from 6-hydroxycaproic acid of formula $HO-(CH_2)_5-COOH$ and/or from esters thereof.

During the contacting step, the precursor is preferably added in an amount up to about 30% by weight, generally from about 0.01% to about 20% by weight of the total weight of the reaction mixture containing the precursor, the peroxygen compound, water and the formed 6-hydroxypercaproic acid.

The peroxygen compound used in this step may be any suitable organic or inorganic peroxygen compound capable of effecting the peroxidation of the precursor to 6-hydroxypercaproic acid. Hydrogen peroxide is particularly preferred as it avoids additional steps, such as neutralisation or partial neutralisation arising with alternative peroxygen compounds like sodium percarbonate or sodium perborate. The peroxygen compound is added in an amount up to about 30% by weight, generally from about 0.01% to about 20% by weight of the total weight of the reaction mixture as defined above.

The reaction between the precursor and the peroxygen compound, e. g. hydrogen peroxide, can be carried out in the absence of an acid catalyst. Alternatively, the reaction can be conducted in presence of a strong acid acting as a catalyst. This strong acid may be a mineral acid or an organic sulphonic acid, such as sulphuric acid, phosphoric acid and methanesulphonic acid, especially sulphuric acid. The acid catalyst is added in an amount of 0.1 to 5% by weight and often in an amount from 0.5 to 2% by weight of the total weight of the reaction mixture. By choosing the higher concentrations of acid catalyst it is possible to enable peroxidation to occur at a convenient rate without the need of elevated reaction temperatures.

The invention process can be carried out at temperatures within the range of from 10 to 50° C. Use of a yet higher temperature tends to accelerate noticeably loss of available oxygen (Avox) from the compositions. In many instances the process is conducted at temperatures around ambient, i. e. between 15 and 30° C., preferably at ambient temperature.

In another variation of the process, the contacting step is followed by an equilibrating step until the concentration of 6-hydroxypercaproic acid approaches its maximum or at least a substantial fraction thereof This can be achieved by monitoring the peracid content of the composition and the proportion of unreacted peroxygen compound, for example by periodic sample analysis.

As stated above, using a suitable concentration of acid catalyst within the range identified hereinbefore, the equilibrating step will take from less than 1 to about 10 days, depending on the nature of the precursor and of the peroxygen compound used to prepare the composition, as well as on the selected temperature. The equilibrating step may be conducted at a temperature within the same range as for the contacting step, preferably also at ambient temperature.

Optional components in the compositions according to the present invention comprise stabilisers and other additives such as catalysts, surfactants, chelating agents, corrosion inhibitors, thickeners, dyes, perfumes, scale removing agents such as mineral or organic acids and the like. The optional components can be present in a wide range of concentrations, but in many cases the total concentration of these components will not exceed 25% by weight of the total weight of the reaction mixture as defined above.

Stabilisers can desirably be employed to improve the storage stability of compositions according to the invention. Suitable stabilisers include hydroxy substituted aromatic carboxylic acids and ester derivatives thereof, particularly phenol carboxylic acids such as p-hydroxybenzoic acid and ester derivatives such as methyl or ethyl esters. They also include organic polyphosphonic acid sequestrants such as ethylidene diphosphonic acid, and aminopolymethylenephosphonic acid, pyridine carboxylic acids, especially dipicolinic acid and mixtures thereof. In addition, inorganic stabilisers may be used. An example of inorganic stabiliser is colloidal tin. These compounds are often incorporated in an amount up to 5% by weight and generally in the range of from 0.025 to 1% by weight of the reaction mixture as defined above. When an acid stabiliser is used, it can also perform as catalyst.

In a further embodiment of the present invention there are provided aqueous percarboxylic acid compositions obtainable by a process of the invention.

In a further embodiment of the present invention there are provided aqueous percarboxylic acid compositions comprising 6-hydroxypercaproic acid and hydrogen peroxide.

Preferably, these compositions comprise up to 20% by weight 6-hydroxypercaproic acid, up to 20% by weight hydrogen peroxide and optionally up to 25% by weight total concentration of one or more stabilisers or other additives such as catalysts, surfactants, chelating agents, corrosion inhibitors, thickeners, dyes, perfumes, scale removing agents and the like.

The composition may be used as such or may be diluted by mixture with water. The extent of dilution is at the discretion of the process operator and depends on the intended use. It is often convenient to dilute until the solution has a peracid concentration in the region of about 0.0001 to 2% by weight. A composition containing such a concentration of peracid represents a ready to use disinfectant composition suitable in industrial and domestic disinfection applications.

The present invention concerns therefore also the use of the above described compositions as disinfectants. The method for disinfection according to the present invention comprises contacting the substrate to be disinfected with the composition. The composition may be employed with or without dilution. When compositions are diluted, dilution is usually chosen to give a 6-hydroxypercaproic acid concentration in solution of between about 1 part per million and 10000 parts per million, depending on the substrate. The disinfecting method can use a wide range of temperatures, typically from about 4° C. to the boiling point of the disinfectant.

The composition of the invention can be used in a range of disinfection applications: e.g. disinfection of microorganism contaminated aqueous media e.g. process waters containing bacteria, algae, yeasts and/or viruses from industries such as paper and pulp, food processing e.g. sugar refining, brewing, wine making, discharges from sewage treatment works, meat processing factories, carcase rendering and livestock rearing. Other substrates include irrigation water in the horticultural industry, contaminated cooling waters, and contaminated surfaces in e.g. food processing, horticulture, catering, domestic or hospital environments. The invention compositions can be used to treat crops and harvested plants or plant products.

It will nonetheless also be recognised that the peracid compositions according to the invention or produced by a process according to the invention may also be employed, if desired, for other purposes for which peracids are used, including bleaching or as a bleach additive in washing processes.

Having described the invention in general terms, specific embodiments thereof will now be illustrated by way of example only.

EXAMPLES 1–4

A range of solutions were prepared at ambient temperature containing 5 or 10% ε-caprolactone (CAPA monomer), 7 or 10% hydrogen peroxide, 1% of $H_2SO_4$, 0.6% 1-hydroxyethane-1,1-diphosphonic acid (HEDP) and water (DMW). 100 g of each sample was prepared and equilibration was done at ambient for 10 days. The samples were then stored in vented polyethylene bottles for 6 weeks at 32° C. and 80% RH. The peracid content and $H_2O_2$ content were measured. The results are shown in Table 1.

TABLE 1

| | | | Equilibration at ambient. | | | | | | | |
|---|---|---|---|---|---|---|---|---|---|---|
| | | | 1 Day | | 3 Days | | 7 Days | | 10 Days | |
| Ex. | Formulation | % | % peracid | % $H_2O_2$ | % peracid | % $H_2O_2$ | % peracid | % $H_2O_2$ | % peracid | % $H_2O_2$ |
| 1 | CAPA Monomer | 5.0 | 0.25 | 7.11 | 0.35 | 7.05 | 0.41 | 7.00 | 0.39 | 7.09 |
| | $H_2O_2$ (as 100%) | 7.0 | | | | | | | | |
| | HEDP (as 100%) | 0.6 | | | | | | | | |
| | $H_2SO_4$ (98%) | 1.0 | | | | | | | | |
| | DMW | 86.0 | | | | | | | | |
| 2 | CAPA Monomer | 10.0 | 0.49 | 7.14 | 0.70 | 6.94 | 0.70 | 6.91 | 0.78 | 7.00 |
| | $H_2O_2$ (as 100%) | 7.0 | | | | | | | | |
| | HEDP (as 100%) | 0.6 | | | | | | | | |
| | $H_2SO_4$ (98%) | 1.0 | | | | | | | | |
| | DMW | 81.0 | | | | | | | | |
| 3 | CAPA Monomer | 10.0 | 0.78 | 9.95 | 1.01 | 9.98 | 1.05 | 9.88 | 1.09 | 9.75 |
| | $H_2O_2$ (as 100%) | 10.0 | | | | | | | | |
| | HEDP (as 100%) | 0.6 | | | | | | | | |
| | $H_2SO_4$ (98%) | 1.0 | | | | | | | | |
| | DMW | 78.0 | | | | | | | | |
| 4 | CAPA Monomer | 5.0 | 0.43 | 9.93 | 0.53 | 10.05 | 0.56 | 9.98 | 0.58 | 9.88 |
| | $H_2O_2$ (as 100%) | 10.0 | | | | | | | | |
| | HEDP (as 100%) | 0.6 | | | | | | | | |
| | $H_2SO_4$ (98%) | 1.0 | | | | | | | | |
| | DMW | 83.0 | | | | | | | | |

| | | Storage at 32° C./80% RH | | | | | | | | |
|---|---|---|---|---|---|---|---|---|---|---|
| | Initial Analysis | | 1 Week | | 2 Weeks | | 4 Weeks | | 6 Weeks | |
| Ex. | % peracid | % $H_2O_2$ | % peracid | % $H_2O_2$ | % peracid | % $H_2O_2$ | % peracid | % $H_2O_2$ | % peracid | % $H_2O_2$ |
| 1 | 0.39 | 7.09 | 0.33 | 6.99 | 0.29 | 6.70 | 0.37 | 6.77 | 0.31 | 6.81 |
| | Recovery | | 85.0% | 98.6% | 75.0% | 94.5% | 95.0% | 95.5% | 80.0% | 96.1% |
| | Total AvOx recovery | | | 98.4% | | 94.3% | | 95.5% | | 95.9% |
| 2 | 0.78 | 7.00 | 0.68 | 6.91 | 0.72 | 6.62 | 0.72 | 6.78 | 0.68 | 6.70 |
| | Recovery | | 87.5% | 98.7% | 92.5% | 94.6% | 92.5% | 96.9% | 87.5% | 95.7% |
| | Total AvOx recovery | | | 98.4% | | 94.5% | | 96.7% | | 95.5% |

TABLE 1-continued

| 3 | 1.09 | 9.75 | 0.94 | 9.93 | 0.90 | 9.50 | 0.99 | 9.67 | 0.97 | 9.59 |
|---|------|------|------|------|------|------|------|------|------|------|
|   | Recovery |  | 85.7% | 101.8% | 82.1% | 97.4% | 91.1% | 99.2% | 89.3% | 98.4% |
|   | Total AvOx recovery |  |  | 101.4% |  | 97.1% |  | 99.0% |  | 98.1% |
| 4 | 0.58 | 9.88 | 0.49 | 10.01 | 0.39 | 9.54 | 0.49 | 9.61 | 0.49 | 9.31 |
|   | Recovery |  | 83.3% | 101.3% | 66.7% | 96.6% | 83.3% | 97.3% | 83.3% | 94.2% |
|   | Total AvOx recovery |  |  | 101.1% |  | 96.2% |  | 97.1% |  | 94.1% |

After 6 weeks storage under these conditions all solutions gave at least 80% peracid recovery, and 90% $H_2O_2$ recovery, based on the initial analysis at ambient.

However, all of the solutions showed little peracid loss from week 1–6, after allowing for drop in peracid level after re-equilibrating the solution at 32° C.

EXAMPLE 5

A solution was made up at ambient temperature containing 7% CAPA monomer, 7% hydrogen peroxide, 1% of sulphuric acid, 0.6% HEDP, 0.2% p-hydroxybenzoic acid (pHBA) and water (DMW). 100 g of the solution was made up and equilibration was done at ambient for 9 days. The sample was then stored in a vented polyethylene bottle for 18 weeks at 32° C. and 80% RH. The peracid content and hydrogen peroxide content were measured. The results are shown in table 2.

TABLE 2

|  |  | Storage at 32° C./80% RH | | | |
|---|---|---|---|---|---|
|  |  | Initial analysis | | 18 weeks | |
| Formulation | % | % peracid | % $H_2O_2$ | % peracid | % $H_2O_2$ |
| CAPA Monomer | 7% |  |  |  |  |
| $H_2O_2$ (as 100%) | 7% |  |  |  |  |
| HEDP (as 100%) | 0.6% | 0.60 | 6.87 | 0.43 | 6.54 |
| $H_2SO_4$ (98%) | 1% |  |  |  |  |
| pHBA | 0.2% | Recovery |  | 71.1% | 95.2% |
| DMW | 71% | Total AvOx recovery |  |  | 94.7% |

EXAMPLES 6–8

Further solutions were prepared as above containing up to 20% ε-caprolactone and 15–20% $H_2O_2$, with dipicolinic acid or 4-hydroxybenzoic acid (pHBA) in addition to HEDP as stabiliser. The results are shown in Table 3.

TABLE 3

|  |  |  | Storage at 32° C./80% RH 20 days after preparation | |
|---|---|---|---|---|
| Example | Formulation | % | % peracid | % $H_2O_2$ |
| 6 | CAPA Monomer | 19 |  |  |
|  | $H_2O_2$ (as 100%) | 19 |  |  |
|  | HEDP (as 100%) | 1.0 | 3.81 | 19.26 |
|  | Dipic. Acid (as 100%) | 0.03 |  |  |
|  | $H_2SO_4$ (98%) | 1 |  |  |
|  | DMW | 59 |  |  |
| 7 | CAPA Monomer | 20 |  |  |
|  | $H_2O_2$ (as 100%) | 15 |  |  |
|  | HEDP (as 100%) | 1.0 | 2.95 | 15.26 |
|  | Dipic. Acid (as 100%) | 0.03 |  |  |
|  | $H_2SO_4$ (98%) | 1 |  |  |
|  | DMW | 62 |  |  |
| 8 | CAPA Monomer | 20 |  |  |
|  | $H_2O_2$ (as 100%) | 20 |  |  |
|  | HEDP (as 100%) | 1 | 4.32 | 18.75 |
|  | Dipic. Acid (as 100%) | 0.04 |  |  |
|  | $H_2SO_4$ (98%) | 1 |  |  |
|  | DMW | 57 |  |  |

These data show that it is possible to generate solutions containing at least 4% peracid in solution.

COMPARISONS 9–12

A range of solutions were prepared at ambient temperature containing 5 or 10% glycolic acid, 7 or 10% hydrogen peroxide, 1% of $H_2SO_4$, 1% HEDP and water (DMW). 100 g of each sample was prepared and equilibration was done at ambient for 7 days. The peracid content and $H_2O_2$ content were measured. The results are shown in Table 4.

TABLE 4

|  |  |  | Equilibration at ambient. | | | | | |
|---|---|---|---|---|---|---|---|---|
|  |  |  | 1 Day | | 3 Days | | 7 Days | |
| Ex. | Formulation | % | % peracid | % $H_2O_2$ | % peracid | % $H_2O_2$ | % peracid | % $H_2O_2$ |
| 9 | Glycolic acid | 5.0 | 0.027 | 7.05 | 0.039 | 7.06 | 0.045 | 7.32 |
|  | $H_2O_2$ (as 100%) | 7.0 |  |  |  |  |  |  |
|  | HEDP | 1.0 |  |  |  |  |  |  |
|  | $H_2SO_4$ (98%) | 1.0 |  |  |  |  |  |  |
|  | DMW | 86.0 |  |  |  |  |  |  |

TABLE 4-continued

| | | Equilibration at ambient. | | | | | |
|---|---|---|---|---|---|---|---|
| | | 1 Day | | 3 Days | | 7 Days | |
| Ex. Formulation | % | % peracid | % $H_2O_2$ | % peracid | % $H_2O_2$ | % peracid | % $H_2O_2$ |
| 10 Glycolic acid | 10.0 | 0.073 | 7.10 | 0.065 | 7.27 | 0.080 | 7.19 |
| $H_2O_2$ (as 100%) | 7.0 | | | | | | |
| HEDP | 1.0 | | | | | | |
| $H_2SO_4$ (98%) | 1.0 | | | | | | |
| DMW | 81.0 | | | | | | |
| 11 Glycolic acid | 10.0 | 0.110 | 10.27 | 0.111 | 10.19 | 0.106 | 10.06 |
| $H_2O_2$ (as 100%) | 10.0 | | | | | | |
| HEDP | 1.0 | | | | | | |
| $H_2SO_4$ (98%) | 1.0 | | | | | | |
| DMW | 78.0 | | | | | | |
| 12 Glycolic acid | 5.0 | 0.052 | 10.21 | 0.058 | 10.17 | 0.059 | 10.20 |
| $H_2O_2$ (as 100%) | 10.0 | | | | | | |
| HEDP | 1.0 | | | | | | |
| $H_2SO_4$ (98%) | 1.0 | | | | | | |
| DMW | 83.0 | | | | | | |

The results of comparisons 9–12 show a substantial decrease in peracid content when compared to Examples 1–4, clearly demonstrating the efficacy of the reaction of ε-caprolactone with $H_2O_2$.

EXAMPLE 13

In this Example, compositions were prepared as described for Examples 6–8 and diluted to the concentrations in Table 5 to evaluate their disinfectant capabilities and to compare them with the performance of disinfectant compositions containing identical concentrations of peracetic acid (Proxitane 0510).

The test protocol used was the CEN Test method prEN 1040:1996 Chemical Disinfectants and Antiseptics—Basic Bactericidal Activity. A 5 minutes contact time was used.

The biocidal activity of 6-hydroxypercaproic acid is shown in comparison to Proxitane 0510 in Table 5.

TABLE 5

| | Concentration mg/l Sample | | | | | | | | | |
|---|---|---|---|---|---|---|---|---|---|---|
| | 2.5 | 5 | 10 | 15 | 20 | 25 | 30 | 50 | 75 | 100 |
| Biocidal Activity of Peracids Against *Escherichia coli* | | | | | | | | | | |
| Proxitane 0510 | | | | | | >5.35 | >5.35 | >5.35 | | |
| | | <4.11 | >5.42 | >5.42 | >5.42 | | | | | |
| CAPA | | | | | >5.05 | | >5.05 | | >5.05 | >5.05 | >5.05 |
| | <4.11 | <4.11 | >5.42 | >5.42 | | | | | | |
| Biocidal Activity of Peracids Against *Staphylococcus aureus* | | | | | | | | | | |
| Proxitane 0510 | | | | | | >5.15 | >5.15 | >5.15 | | |
| | | <4.05 | <4.05 | 4.03 | >5.36 | | | | | |
| CAPA | | | | | >5.05 | | >5.05 | | >5.05 | >5.05 | >5.05 |
| | <4.05 | <4.05 | 4.71 | >5.36 | | | | | | |

Figures shown are logarithmic reduction factors (LRF) for the organism at given concentrations
>5 = CEN Pass The test exhibit a good level of biocidal performance of the compositions of the present invention, i.e. a reduction of the concentration of *S. aureus* and *E. coli* by about $10^5$ at peracid concentrations of only 10 mg/l.

What is claimed is:

1. A compound of formula HO—$(CH_2)_5$—$CO_3$H.

2. A process for preparing an aqueous percarboxylic acid composition, comprising
   contacting a precursor compound of formula HO—$(CH_2)_5$—$CO_3$H with a peroxygen compound.

3. The process according to claim 2, wherein the precursor is selected from the group consisting of ε-caprolactone, an oligomer of ε-caprolactone, a dimer of ε-caprolactone and mixtures thereof.

4. The process according to claim 2, wherein the precursor is 6-hydroxycaproic acid of formula HO—$(CH_2)_5$—COOH, an ester thereof or mixtures thereof.

5. The process according to claim 2, wherein the precursor is added in an amount of up to 20% by weight.

6. The process according to claim 2, wherein the peroxygen compound is added in an amount of up to 20% by weight.

7. The process according to claim 2, wherein the peroxygen compound is hydrogen peroxide.

8. The process according to claim 2, wherein the precursor compound is contacted with the peroxygen compound in the presence of an acid catalyst.

9. The process according to claim 8, wherein the acid catalyst is present in an amount of from 0.1 to 5% by weight.

10. The process according to claim 8, wherein the acid catalyst is sulphuric acid.

11. The process according to claim 2, wherein contacting is followed by equilibrating until the concentration of compound of formula HO—$(CH_2)_5$—$CO_3H$ approaches a maximum.

12. The process according to claim 11, wherein equilibrating takes from less than 1 to 10 days.

13. The process according to claim 11, wherein equilibrating is conducted at ambient temperature.

14. The process according to claim 2, further comprising adding one or more additives chosen from the group consisting of stabilisers, catalysts, surfactants, chelating agents, corrosion inhibitors, thickeners, dyes, perfumes, scale removing agents and mixtures thereof.

15. The process according to claim 14, wherein the stabiliser is present in a concentration up to 5% by weight.

16. The process according to claim 14, wherein the stabiliser is chosen from the group consisting of 1-hydroxyethane-1,1-diphosphonic acid, dipicolinic acid, 4-hydroxybenzoic acid and mixtures thereof.

17. An aqueous percarboxylic acid composition obtained by the process according to claim 2.

18. An aqueous percarboxylic acid composition comprising a compound of formula HO—$(CH_2)_5$—$CO_3H$ and hydrogen peroxide.

19. The aqueous percarboxylic acid composition according to claim 18, comprising up to 20% by weight a compound of formula HO—$(CH_2)_5$—$CO_3H$ and up to 20% by weight hydrogen peroxide.

20. The aqueous percarboxylic acid composition according to claim 17, further comprising one or more additives selected from the group consisting of stabilisers, catalysts, surfactants, chelating agents, corrosion inhibitors, thickeners, dyes, perfumes, scale removing agents and mixtures thereof.

21. A disinfectant comprising the aqueous percarboxylic acid composition claimed in claim 17.

22. A bleaching agent comprising the aqueous percarboxylic acid composition claimed in claim 17.

23. The process as claimed in claim 14, wherein the scale removing agent is a mineral acid or an organic acid.

24. The aqueous percarboxylic acid composition claimed in claim 20, wherein the scale removing agent is a mineral acid or an organic acid.

* * * * *